United States Patent
Yoneya

(10) Patent No.: US 9,526,414 B2
(45) Date of Patent: Dec. 27, 2016

(54) METHOD FOR DIAGNOSING GLAUCOMA BY OBSERVING CONNECTIVE TISSUE OF LAMINA CRIBROSA

(71) Applicants: Shin Yoneya, Maebashi-shi (JP); Hiroto Kuroda, Tokyo (JP)

(72) Inventor: Shin Yoneya, Maebashi (JP)

(73) Assignees: Shin Yoneya, Maebashi-Shi (JP); Hiroto Kuroda, Tokyo (JP)

( * ) Notice: Subject to any disclaimer, the term of this patent is extended or adjusted under 35 U.S.C. 154(b) by 147 days.

(21) Appl. No.: 14/285,788

(22) Filed: May 23, 2014

(65) Prior Publication Data

US 2015/0335236 A1    Nov. 26, 2015

(51) Int. Cl.
A61B 3/00    (2006.01)
A61B 3/10    (2006.01)
A61B 3/14    (2006.01)

(52) U.S. Cl.
CPC ........ *A61B 3/102* (2013.01); *A61B 3/14* (2013.01)

(58) Field of Classification Search
CPC .................................. A61B 3/10; A61B 3/00
USPC ................... 351/246, 206, 221, 205; 600/476
See application file for complete search history.

(56) References Cited

U.S. PATENT DOCUMENTS

2010/0160789 A1*  6/2010  Dilworth .............. A61B 3/0025
                                                      600/476

* cited by examiner

*Primary Examiner* — Hung Dang
(74) *Attorney, Agent, or Firm* — Hamre, Schumann, Mueller & Larson, P.C.

(57) ABSTRACT

A method for diagnosing the probability of the onset of glaucoma or the degree of the advancement of glaucoma by observing connective tissue of lamina cribrosa and its neighboring part of retina, namely the movable nature of lamina cribrosa in relation to retina.

6 Claims, 7 Drawing Sheets

Normal glaucoma f < F

METHOD FOR DIAGNOSING GLAUCOMA BY OBSERVING CONNECTIVE TISSUE OF LAMINA CRIBROSA

BACKGROUND

In the past, glaucoma was regarded as a disease causing characteristic optic nerve disablement (optic nerve damage) due to ocular hypertension. However, an epidemiological research ("the Tajimi study") conducted from 2000 to 2001 has revealed that the prevalence rate of normal-tension glaucoma (normotensive glaucoma) is significantly higher than that of hypertension glaucoma (high-tension glaucoma) in Japan compared with the Western countries. At present, glaucoma is defined as "a disease that involves distinctive changes in optic disc and the visual field and is marked by functional and structural abnormalities (disorders) in the eye in which optic nerve damage can ordinarily be alleviated and inhibited by sufficiently reducing intra-ocular pressure" (the Japan Glaucoma Society Guidelines for Glaucoma (3rd Edition)). Therefore, at present, the main purpose of glaucoma treatment is to reduce intra-ocular pressure. In addition, there have been attempts to develop neuroprotective agents in recent years. However, treatment of glaucoma involving the reduction of intra-ocular pressure has limitations. Thus, glaucoma is the leading disease in terms of the certification of physical disability caused by visual impairment in Japan.

Regarding glaucoma in the Western countries, the prevalence rate of high-tension glaucoma has been higher than that of normal-tension glaucoma and thus there has been little attention to normal-tension glaucoma. In the history of glaucoma, the possibility of the presence of normal-tension glaucoma was suggested. For example, "Duke-Elder's System of Ophthalmology" published in 1969 recites as follows: "It is to be remembered that an intra-ocular pressure that is generally accepted as being within the normal range may produce the typically pathological effects at the optic disc and in the visual fields when the nerve head is unduly vulnerable and may occur, for example, in myopic eyes; these cases properly come under the definition of glaucoma." It is suggested that the reason for the high prevalence rate of normal-tension glaucoma in Japan is associated with myopia. However, there has been no specific explanation why optic disc is "fragile" in patients with myopia.

Optic Nerve Structure and Optic Disc Structure

Light enters into the eye and then is received by visual cells (the first neurons) so as to be converted into signals. The signals are further transmitted from bipolar cells (the second neurons) to ganglion cells. Axis cylinders of the ganglion cells serve as optic nerve fibers (the third neurons). The optic nerve fibers form a fascicle and the fascicle extends from optic disc outside the eye for signal transmission to the visual center of the brain.

Optic disc has a relatively oblong elliptical shape with a diameter of about 1.6 mm and is positioned on the nasal side of macula lutea (limbus luteus). About 1,200,000 axis cylinders of ganglion cells form a fascicle of optic nerve fibers such that the fascicle extends outside the eye. In addition, the central retinal artery and vein also extend through optic disc. When the fascicle of optic nerve fibers extends outside the eye, the optic nerve fibers run through 500-600 lamina pores of lamina cribrosa formed with connective tissue. When viewed from the exterior of the eye, the optic nerve is positioned on the nasal side of the eyeball in a horizontal view.

FIG. 2 shows a general image of a fascicle of optic nerve fibers extending through lamina cribrosa obtained by histological examination or scanning microscopic observation. However, there has been no literature about the anatomical role of lamina cribrosa as well as the morphological details thereof.

SUMMARY OF THE INVENTION

The inventors of this invention developed femto second mode-lock type optical coherence tomography (OCT) using a laser as a light source, which is disclosed in Suzuki M, Baba M, Yoneya S and Kuroda H. Efficient special broadening of Supercontinuum in photonic crystal fiber with self-phase modulation induced by femtosecond laser pulse, Applied Physics Letters 101. 191110 (2012). The present inventors further succeeded in three-dimensionally observing lamina cribrosa of the living eye by the OCT. Accordingly, the present inventors elucidated the mechanism of the onset of glaucoma by comparing normal eyes and glaucoma eyes and revealed that changes in connective tissue of lamina cribrosa caused by aging of optic disc and continuous mechanical stimulation are associated with the primary lesion of glaucoma. The above findings have led to the completion of the present invention.

The present invention relates to a method for diagnosing the primary lesion of glaucoma by observing lamina cribrosa to determine the degree of movability of the lamina cribrosa with respect to the retina surface.

DETAILED DESCRIPTION OF THE EMBODIMENT

Figure 1:
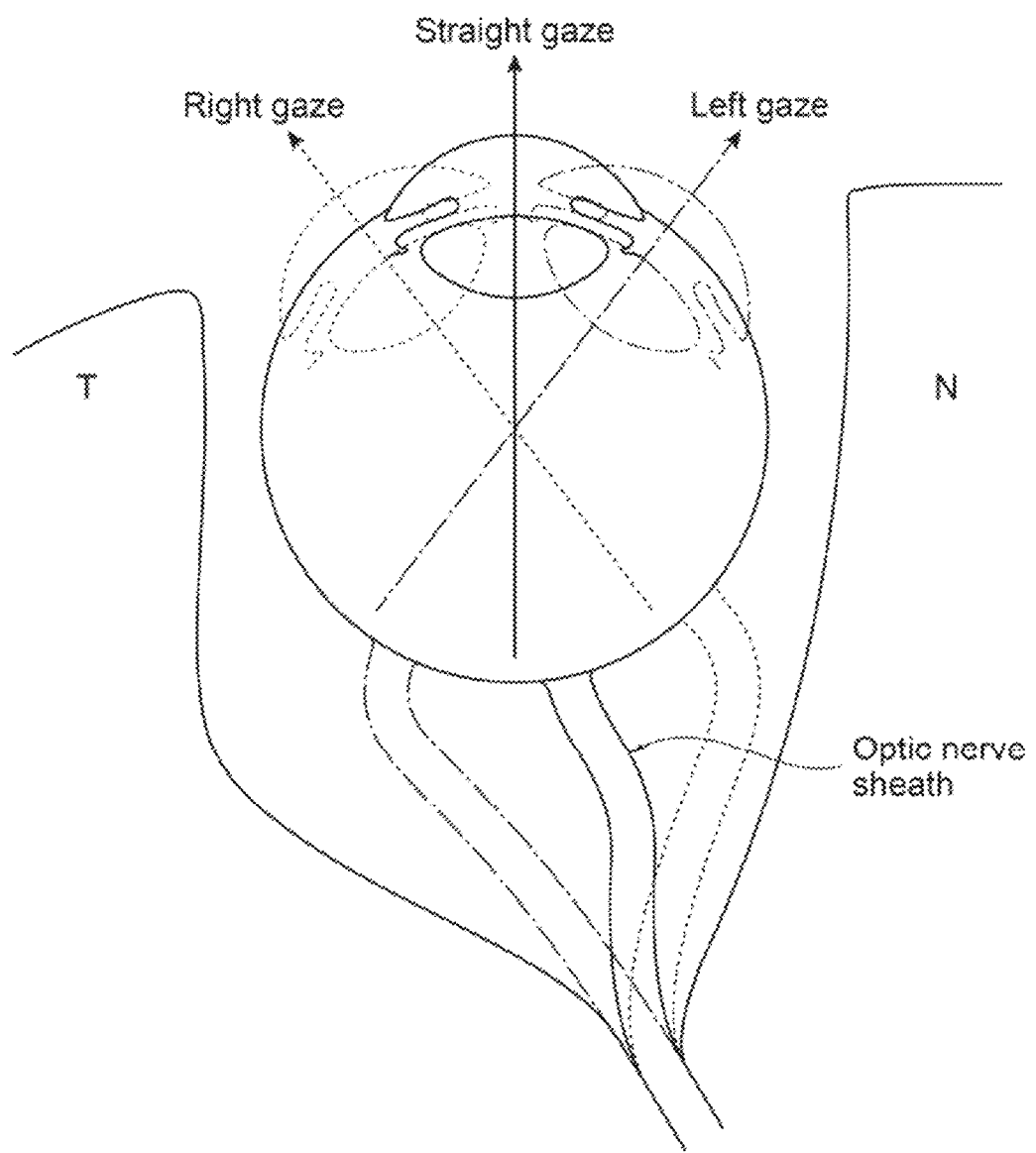
FIG. 1 conceptually illustrates the eyeball movement in the orbit and the movement of the retrobulbar optic nerve.
Figure 2:
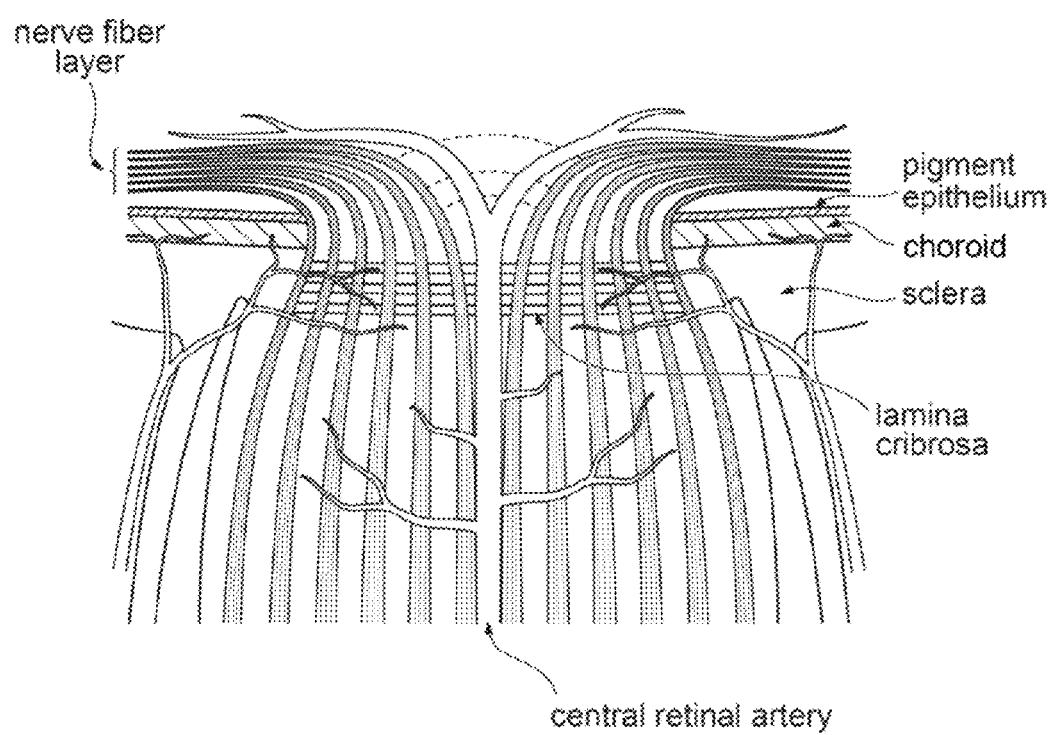
FIG. 2 conceptually illustrates the optic disc.

The eyeball is positioned within the orbit and dynamically moves up and down and from side to side within the orbit. This is referred to as the eyeball movement. When the eyeball moves from side to side, the retrobulbar optic nerve attached to the eyeball dynamically moves like a whip as shown in FIG. 1. FIG. 2 shows optic disc which is the site where the nerve fibers of the retina are concentrated. Given that optic nerve fibers that form a fascicle run through cylindrically shaped lamina pores, the optic nerve fibers move inside the eye as the optic nerve which is a fascicle of optic nerve fibers dynamically moves outside the eye. However, in fact, it has not been verified yet. This is probably because lamina cribrosa has a hub-like structure such that the movement of the fascicle of optic nerve fibers outside the eye is not transmitted to the optic nerve fibers inside the eye. The present inventors consider that the role of lamina cribrosa that functions as a hub is closely related to the fragility of optic disc.

Figure 3:
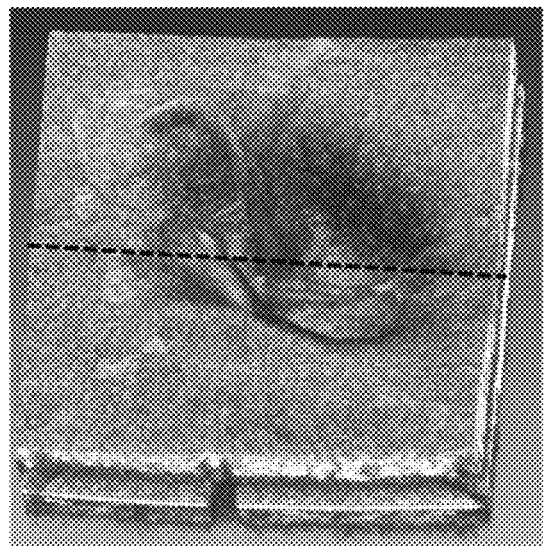
FIG. 3 shows a three-dimensional image of the optic disc taken by optical coherence tomography.
Figure 4:
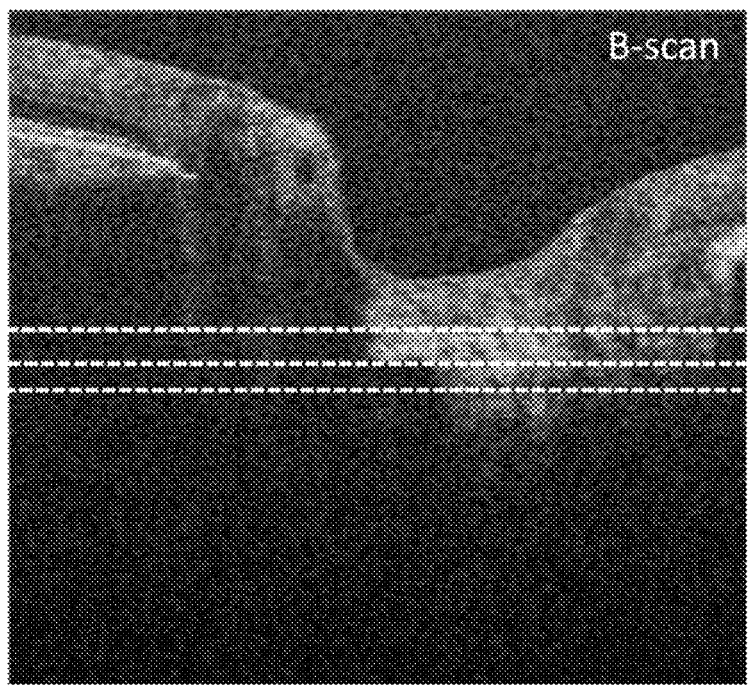
FIG. 4 shows a cross section along the dashed line B-scan of FIG. 3.
Figure 5A:
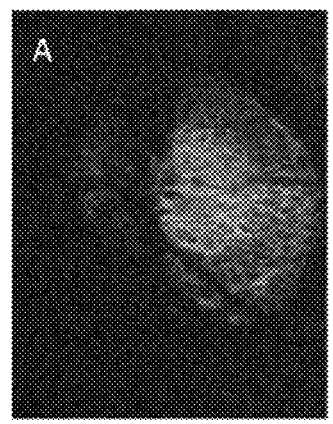
FIG. 5A shows a cross section along the dashed line A in FIG. 4.
Figure 5B:
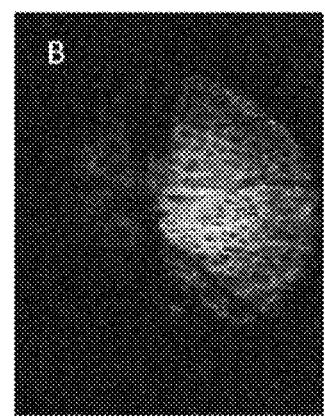
FIG. 5B shows a cross section along the dashed line B of FIG. 4.
Figure 5C:
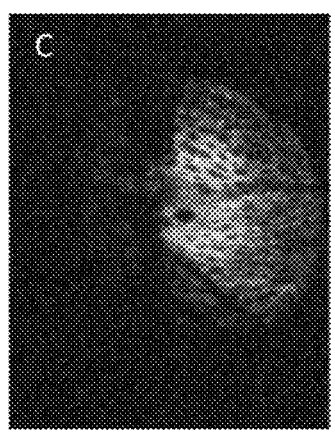
FIG. 5C shows a cross section along the dashed line C of FIG. 4.

As a result of the observation by OCT conducted by the present inventors, it has been revealed that lamina cribrosa has lamina pores with complicated shapes as shown in FIG. 3. FIG. 4 shows a cross section along the dashed line B-scan of FIG. 3. The lamina pore shape observed inside the eye differs from that observed outside the eye as shown in FIG. 4. In FIG. 4, cross sections along the dashed lines A, B, and C correspond to different depths of lamina cribrosa. FIG. 5A shows a cross section along the dashed line A, FIG. 5B shows a cross section along the dashed line B, and FIG. 5C shows a cross section along the dashed line C. Here, it is observed that the mesh structure of the lamina cribrosa varies depending on the depth of a cross section of lamina cribrosa.

Figure 8A:
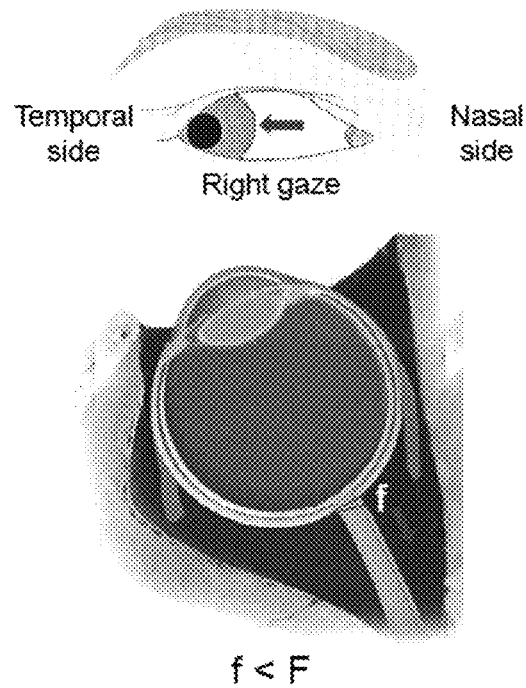
FIG. 8A conceptually shows the movement of the eyeball and optic nerve when the eyeball is at the outwardly displaced position.
Figure 8B:
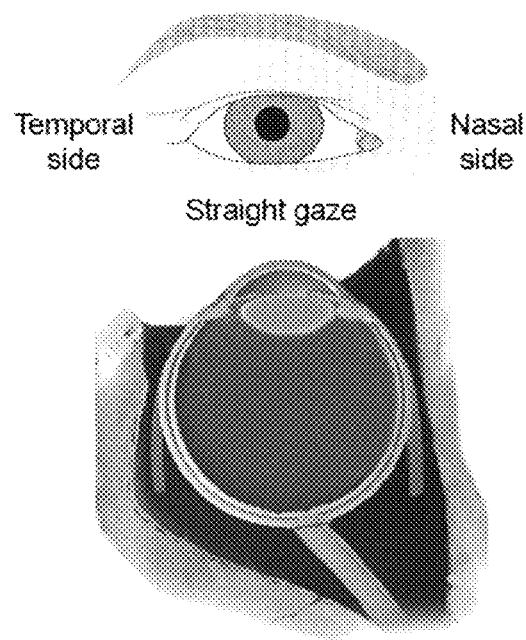
FIG. 8B shows the same when the eyeball is at the center position.
Figure 8C:
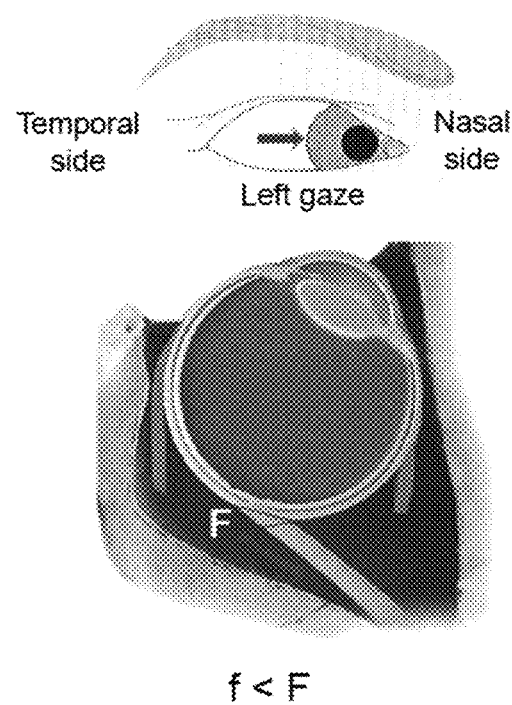
FIG. 8C shows the same when the eyeball is at the inwardly displaced position.

FIGS. 8A to 8C show the positional relationship between the eyeball and optic nerve fibers when the eyeball is at the outwardly displaced position, the same when the eyeball is at the center position, and the same when the eyeball is at the inwardly displaced position, respectively. A horizontal sectional view of the eyeball shows that the optic disc is positioned on the nasal side. This suggests that the amount of change (the amount of movement) of the fascicle of optic nerve fibers when the eyeball is at the inwardly displaced position is greater than that when the eyeball is positioned at the outwardly displaced position, which results in the relationship f<F between stress f generated in the optic disc when the eyeball is positioned at the outwardly displaced position (see FIG. 8A) and stress F generated in the optic disc when the eyeball is positioned at the inwardly displaced position (see FIG. 8C). Thus, the eyeball movement always causes a friction between lamina pores and the fascicle of optic nerve fibers with aging. If the intra-ocular pressure is high, this friction would further increase. Changes with aging and factors such as constitutional factors and intra-ocular pressure affect the strength of connective tissue that constitutes the lamina cribrosa. In addition, it is presumed that this chronic and mechanical stimulation induces weak inflammation so as to cause the release of cytokines which act on the blood vessel walls in optic nerves to cause circulatory disorder such as vascular occlusion.

As a result, optic nerve fibers, which extend on the temporal side inside the optic disc or lamina cribrosa, tend to have damage. This would be associated with the onset of a disorder such as the narrowed visual field or excavation of the optic nerve head observed on the nasal side.

Figure 6:
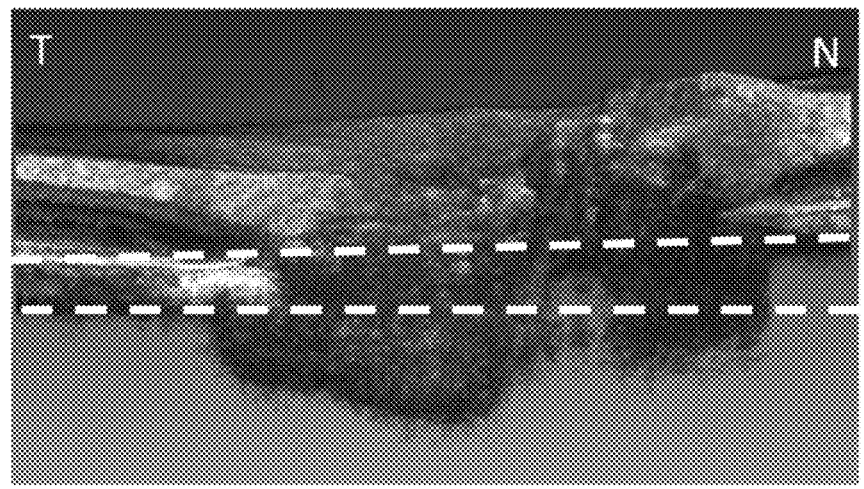
FIG. 6 shows lamina cribrosa of the normal eye.
Figure 7:
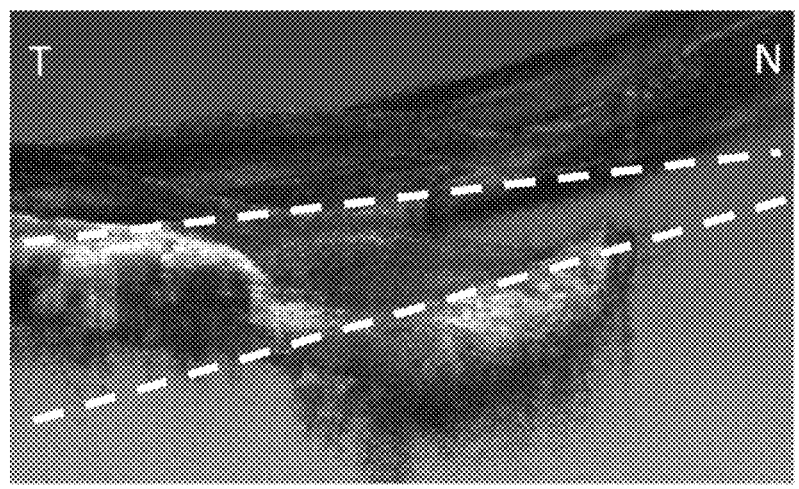
FIG. 7 shows lamina cribrosa of the glaucoma eye.

Continuous application of mechanical stimulation causes lamina cribrosa to have movability which is observed as an early change in glaucoma. This mechanical stimulation results in increased stress on the temporal side and thus causes a significant change in connective tissue on the temporal side since the optic disc is positioned on the nasal side in the horizontal sectional view. The present inventors have found that the lamina cribrosa of the normal eye is positioned such that it intersects the optic disc in parallel with the retina surface as shown in FIG. 6, while on the other hand, the lamina cribrosa of the glaucoma eye has a gradient such that it is positioned far from the retina surface on the temporal side while it is positioned close to the retina surface on the nasal side as shown in FIG. 7.

Based on the above new findings, glaucoma is defined as a disease which is basically induced by aging of optic disc and changes in connective tissue due to continuous friction and is aggravated by elevation of intra-ocular pressure.

Therefore, it is possible to diagnose the probability of the onset of glaucoma and the degree of the advancement of glaucoma by observing condition of connective tissue of lamina cribrosa. A preferred method for observing condition of connective tissue is a method wherein lamina cribrosa is observed based on an OCT image.

What is claimed:

1. A method for diagnosing onset of glaucoma in a subject, which comprises observing an eye of a subject, and evaluating a degree of movability of a lamina cribrosa from a retina of the eye, wherein a gradient of the lamina cribrosa to the retina surface is indicative of the onset of glaucoma.

2. The method according to claim 1, wherein the onset of glaucoma of a subject is diagnosed when the lamina cribrosa has a gradient such that it is positioned far from the retina surface on the temporal side while it is positioned close to the retina surface on the nasal side.

3. The method according to claim 1, wherein an image is obtained by carrying out femto second mode-lock type optical coherence tomography using a laser as a light source and used for the observing.

4. A method for diagnosing a degree of progression of glaucoma of a subject, which comprises observing the degree of movability of a lamina cribrosa from retina, wherein a gradient of the lamina cribrosa to the retina surface is indicative of the degree of the progression of glaucoma.

5. The method according to claim 4, wherein the degree of the progression of glaucoma of a subject is diagnosed when the lamina cribrosa has a gradient such that it is positioned far from the retina surface on the temporal side while it is positioned close to the retina surface on the nasal side.

6. The method according to claim 4, comprising wherein a condition of connective tissue of lamina cribrosa is carried out on image obtained by carrying out femto second mode-lock type optical coherence tomography using a laser as a light source.

* * * * *